United States Patent [19]

Fisher et al.

[11] 3,954,815

[45] May 4, 1976

[54] GLYCIDOL AND GLYCEROL PROCESS

[75] Inventors: Warren C. Fisher, Darien, Conn.;
Seymour M. Linder, Baltimore, Md.; Ralph L. Pelley, Linthicum Heights, Md.; Hsiang-Peng Liao, Glen Burnie, all of Md.

[73] Assignee: FMC Corporation, Philadelphia, Pa.

[22] Filed: May 22, 1970

[21] Appl. No.: 41,675

Related U.S. Application Data

[63] Continuation-in-part of Ser. No. 519,841, Jan. 11, 1966, abandoned.

[52] U.S. Cl. .................................. 260/348.5 L
[51] Int. Cl.² .................................. C07D 301/14
[58] Field of Search ............ 260/348.5 L, 653, 846

[56] References Cited

UNITED STATES PATENTS 2,977,374   3/1961   Phillips et al ................. 260/348.5 L Primary Examiner—Norman S. Milestone

[57] ABSTRACT

This application discloses a process for manufacturing glycidol, and, if desired, glycerol, by epoxidizing allyl alcohol with a 5 to 40% solution of peracetic acid in a substantially anhydrous, inert, organic solvent to produce glycidol in high yield and purity. Formation of by-products is minimized by rapid removal of co-product acetic acid. The glycidol can then be hydrolyzed to form a readily purifiable glycerol.

5 Claims, 3 Drawing Figures

FIG. I.

INVENTORS
WARREN C. FISHER
SEYMOUR M. LINDER
RALPH L. PELLEY
HSIANG-PENG LIAO
BY

GLYCIDOL AND GLYCEROL PROCESS

CROSS REFERENCES TO RELATED APPLICATIONS

This application is a continuation-in-part of U.S. patent application Ser. No. 519,841, filed Jan. 11, 1966, now abandoned.

BACKGROUND OF THE INVENTION:

1. Field of the Invention

This application discloses a process for epoxidizing allyl alcohol with peracetic acid in an essentially anhydrous, inert, organic solvent, and hydrolyzing the epoxidized reaction product, glycidol, to form glycerol. When desired, the hydrolysis step can be omitted and glycidol can be recovered as product.

2. Description of the Prior Art

Glycerol is manufactured from allyl alcohol by two principal processes: chlorohydrination followed by hydrolysis of the intermediate "glycerol chlorohydrin," and by hydroxylation with hydrogen peroxide. Both processes involve difficulties in refining the glycerol to obtain a product of marketable quality. U.S. Pat. No. 2,960,447, for example, discloses a detailed procedure involving multiple distillations at controlled pH as a way to purify glycerol derived from allyl alcohol hydroxylation.

Epoxidations of unsaturated organic compounds by organic peracids are generally conducted with one reactant present in a substantial excess in order to obtain acceptable reaction rates and efficiencies. Epoxidation of low molecular weight unsaturated organic compounds, such as allyl alcohol, with organic peracids produces undesirable by-products because of reaction of the epoxide in the presence of the carboxylic acid co-products.

A method of avoiding these difficulties is suggested by British Pat. No. 837,464 which reacts allyl alcohol and hydrogen peroxide in an aqueous solution, the pH of which is controlled by a minor concentration of an inorganic or organic alkaline-reacting substance. This patent suggests using organic compounds, notably amines, which impart to an aqueous solution an alkaline pH, as the preferred means for accomplishing this end. The reaction of the peroxide with allyl alcohol produces glycidol in a dilute aqueous reaction medium containing catalyst and the added amine; although the glycidol can be converted to glycerol by heating such a mixture, isolation of pure glycidol becomes a difficult problem. This British specification discusses the art-recognized problem of epoxidizing unsaturated compounds with organic peracids, that is, that considerable by-product formation occurs with a diminished yield of epoxide.

German Pat. No. 1,081,462, describes epoxidation of high molecular weight unsaturated materials with percarboxylic acids in a diluent (using reduced temperature and pressure to distill acetic acid and volatile materials away from the reaction mixture.) The process operates under conditions such that acetic acid and volatile materials are continuously distilled away from the mixture. This process is not suitable for the epoxidation of allyl alcohol as allyl alcohol is more volatile than either peracetic or acetic acids and is therefore removed from the reaction zone before any substantial conversion to glycidol occurs.

SUMMARY OF THE INVENTION

We have now discovered a process for manufacturing glycidol, and, if desired, glycerol in high yields and purity comprising: (a) epoxidizing allyl alcohol in a reaction zone at a temperature of 25° to 100°C. using peracetic acid in solution in a substantially anhydrous, inert organic solvent containing between 5 and 40% peracetic acid, the ratio of allyl alcohol to peracetic acid being between 5 and 0.7 moles of allyl alcohol per mole of peracetic acid, until at least 70 to about 95% of the reactant present in less than stoichiometric amount is reacted to form a mixture of glycidol, solvent, co-product acetic acid, allyl alcohol, peracetic acid and some high boiling impurities; (b) subjecting the reaction mixture to a sequence of distillations to rapidly and continuously separate acetic acid from glycidol and then recover glycidol as a distillate; (c) subsequently hydrolyzing glycidol to glycerol using 10 to 100 moles of water per mole of glycidol at a temperature between 20° and 180°C. and recovering glycerol.

Where desired, glycidol may be obtained in high yields by omitting the hydrolysis step and simply recovering glycidol. The glycidol may be recovered from the mixture of reaction products as a commercial product which can be used as a chemical intermediate. This high quality glycidol can also be hydrolyzed to produce an aqueous glycerol which can be purified without employing the extensive refining procedures heretofore encountered in the synthetic production of pure glycerol by prior art processes.

DESCRIPTION OF THE PREFERRED EMBODIMENT

Figure 1:
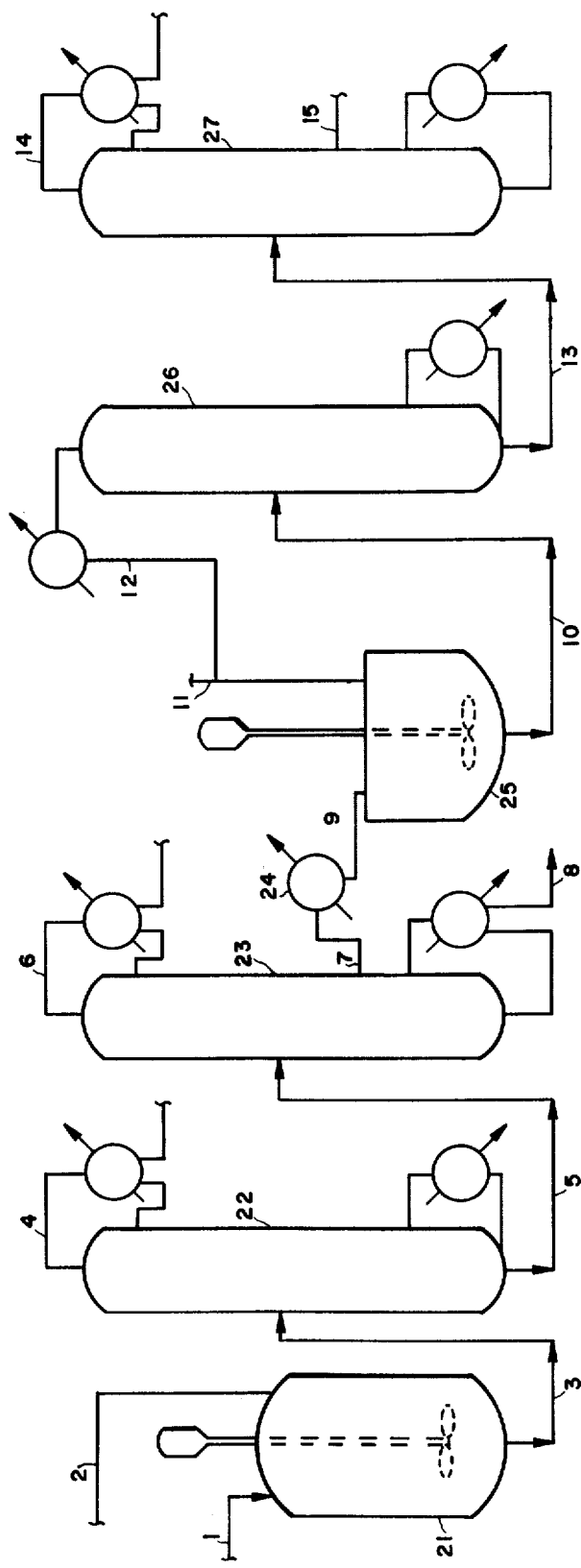
FIG. 1 is a schematic diagram for the overall process using a low boiling solvent and no diluent.

The epoxidation of allyl alcohol by peracetic acid may be a batch or a continuous process. An excess of one reactant is desirable in order to increase the reaction rate. Allyl alcohol is preferred as the reactant to be used in excess, since allyl alcohol is more readily recoverable than peracetic acid.

Peracetic acid is used in solution in a substantially anhydrous, inert, solvent, preferably a ketone, ester or aromatic hydrocarbon whose boiling point may vary from about 45° to about 180°C. Other solvents can also be used, the primary requirement being that they be inert to peracetic acid as well as to glycidol and acetic acid under the conditions employed. The solvent should be separable from allyl alcohol and acetic acid by distillation or other reasonable methods. The solvent should either be substantially lower boiling than glycidol and easily separable therefrom or should form an azeotropic mixture with glycidol, or be higher boiling than glycidol if non-azeotropic. Solvents forming azeotropes with glycidol are of particular value. Various solvents meet these requirements, for example, acetone, ethyl acetate, o-xylene, pseudocumene, monochlorobenzene, ortho-dichlorobenzene, diisobutyl ketone, butyl butyrate, methyl ethyl ketone, isopropyl acetate, methylal, dioxane and halogenated solvents containing not more than six carbon atoms such as chloroform, carbon tetrachloride, perchloroethylene, and fluorinated alkanes. Particularly preferred solvents are acetone, pseudocumene and diisobutyl ketone.

Generally, the peracetic acid content of the solution is between 5 and 40%, this upper limit being a consequence of the explosion hazard associated with too highly concentrated peracetic acid. Peracetic acid concentrations below 5% can be used, however, such dilutions are unattractive in a commercial operation. As a consequence of its preparation the peracetic solution will usually contain a small amount of acetic acid, e.g., 5 to 10% is a common tolerable amount.

The rate at which the allyl alcohol is epoxidized increases with increasing temperatures. For best operation of the process temperature may be between about 25° and 100°C., and is preferably between about 40° and 65°C. Although elevated pressures can be employed to make possible operation at temperatures above the normal boiling point of the system, no overall advantage follows as the reaction is preferably conducted at atmospheric pressure. Variation of the reaction rate with temperature is illutrated by the 40 hours required for completion of the reaction at room temperature, as compared with completion in a period between 2½ to 4 hours at 60°C., when the process is operated as a batch process.

We have found that the reaction rate decreases sharply as the percent conversion of the minor reactant increases to a level above 75%, and particularly above 85%. The reaction carried out at 45°C., using 3:1 molar ratio of allyl alcohol to peracetic acid, results in 90% peracetic acid conversion in 3.5 hours. After 5 hours the conversion is about 93%. In most cases nearly quantitative yields of glycidol based on allyl alcohol are obtained.

Due to these diminishing reaction rates, it is preferable to terminate the epoxidation reaction at some point prior to exhaustion of either of the reactants and to further epoxidize in a second stage. We have found that residual peracetic acid and allyl alcohol further react in the glycidol separation unit. This is utilized advantageously to accomplish a second stage epoxidation in the glycidol separation unit, and, in effect, combine this operation with the glycidol purification. Although the percentage conversion to which the epoxidation reaction is carried in the first stage varies depending upon the reaction conditions and equipment utilized, it is preferred that it should be within the range of between about 70 and 95% of the minor reactant.

Various process options are available. The process, for example, may be operated using a low boiling solvent with no diluent, a low boiling solvent with the addition of another solvent which acts as a diluent, or a high boiling solvent alone.

The process for the preparation of glycerol using a low boiling solvent is described with reference to FIG. 1. Allyl alcohol is fed through line 1 to reactor 21, Peracetic acid at 5 to 40% and preferably 15–25% weight concentration in a substantially anhydrous, inert, solvent, such as ethyl acetate or acetone, is fed through line 2 to reactor 21, where the reaction mixture is maintained at a temperature between 35° and 70°C. The peracetic acid solution usually contains 5–10% of acetic acid. The crude mixture of reaction products containing glycidol is drawn through line 3 and fed to distillation column 22 which is maintained at reduced pressure. The organic solvent is vaporized and removed through line 4.

In the column we prefer, when using acetone as the solvent, to maintain the vapor temperature at about 24°C., the bottom of column 22 operating at 170 mm. of Hg. will be at a temperature of about 80°C. with an underflow composed of acetic acid, glycidol and a small amount of the solvent. This mixture is withdrawn through line 5 and fed rapidly and continuously to column 23 operating at a low overhead pressure, e.g., about 17mm. of Hg. Acetic acid and unreacted allyl alcohol are removed through line 6 at a vapor temperature of about 29°C. The lower section of the column operating at about 65°C. collects high boiling materials (acetins, glycidol polymerization products, etc.) which are removed as an underflow through line 8 and product glycidol is removed at an intermediate stage through line 7 and condensed in condenser 24. When glycidol is removed through line 7 the reboiler temperature is above 120°C.

Reaction between glycidol and acetic acid is minimized by operating so that once the solvent is removed in column 22 the products acetic acid and glycidol are rapidly and continuously separated at as low a temperature as is practicable.

The glycidol may also be removed through line 8 as an impure product, with a reboiler temperature of 65° to 90°C. In this case it can be purified in a second distillation column, not illustrated, placed between column 23 and condenser 24.

The product glycidol is then fed through line 9 to a hydrolyzer 25, where water is supplied through line 11, and temperature is maintained at about 100°C. A 10 to 20% solution of glycerol in water is drawn off through line 10 and fed to a concentrator, 26. Water from the concentrator 26 is recycled to hydrolyzer 25 through lines 12, and 11. Glycerol containing 1 to 2% water is taken from evaporator 26 through line 13 and fed to column 27 operating at 5 mm. Hg., where light impurities are taken from the head through line 14. Pure glycerol is removed as a vapor through line 15.

Figure 2:
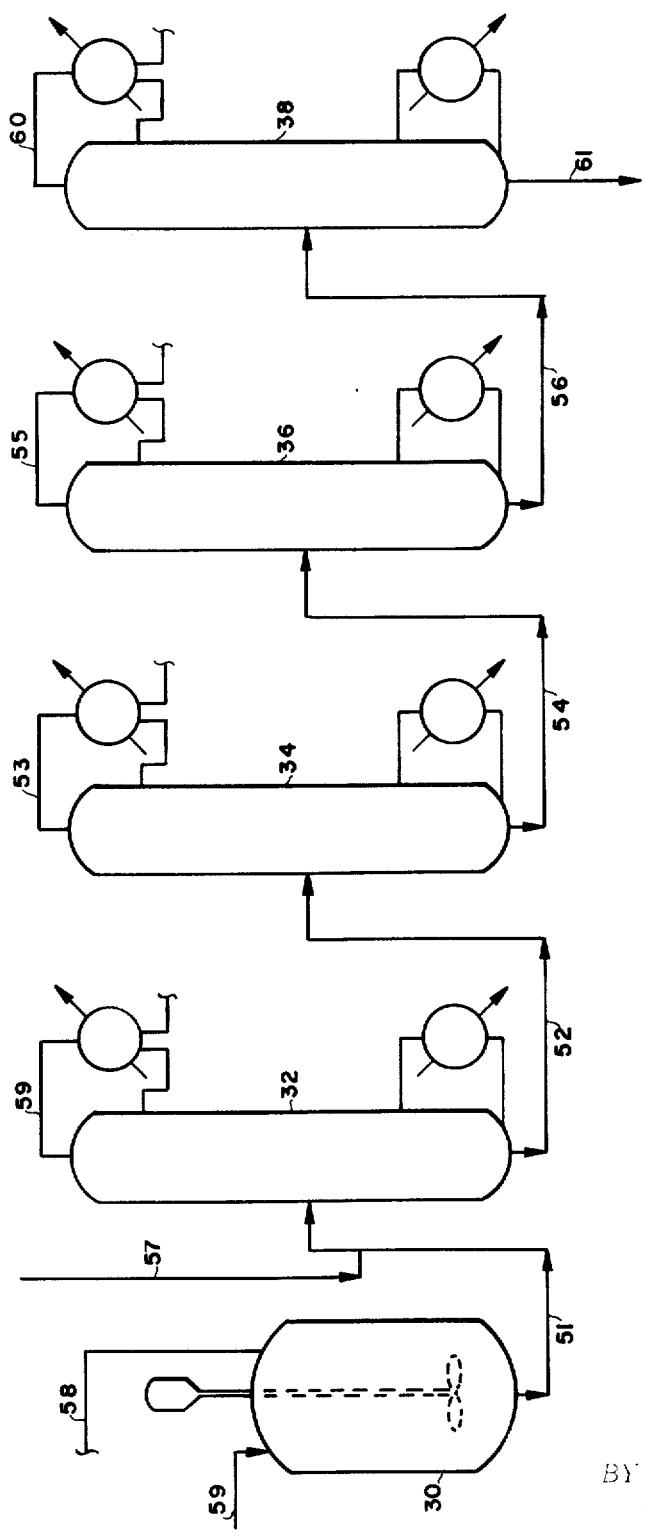
FIG. 2 is a schematic diagram for the process using a low boiling solvent and a diluent, but omitting the hydrolysis step.

The process for the preparation of glycerol or glycidol using a low boiling solvent and diluent is described with reference to FIG. 2. Allyl alcohol is fed through line 59 to reactor 30. Peracetic acid at 5 to 40% and preferably 15 to 25% weight concentration in substantially anhydrous, inert, solvent, such as ethyl acetate or acetone, if fed through line 58 to reactor 30, where the reaction mixture is maintained at a temperature between 35 and 70°C. The peracetic acid solution usually contains 5–10% peracetic acid. The diluent, such as xylenes, monochlorobenzene, ethylbenzene, pseudocumene or diisobutyl ketone, is introduced with or near the epoxidation feed to column 32. The diluent is preferably added through line 57 to the feed line 51 just prior to the entry of the feed line into column 32 which is maintained at reduced pressure. The organic solvent is vaporized and removed through line 59. When acetone is used as the solvent, column 32 is operated at an overhead pressure of about 130mm. Hg.

The low boiling solvent such as acetone, passes overhead and the underflow, also containing the diluent, is then fed through line 52 to column 34 from which allyl alcohol, acetic acid and traces of peracetic acid are taken overhead. Pressure at the top of the column is maintained at about 50 mm. of Hg., the temperature of the overhead vapor at about 50°C. and the reboiler at about 90°C. Some diluent may go overhead with the allyl alcohol, acetic acid and traces of peracetic acid.

Reaction between glycidol and acetic acid is substantially prevented by the fact that in column 34 the products acetic acid and glycidol are rapidly and continuously separated. Glycidol and diluent are withdrawn from the lower portion of column 34 and fed to column 36.

Many diluents, such as pseudocumene, form an azeotropic mixture with glycidol so that an azeotropic composition can be removed overhead from column 36. This actually constitutes an advantage since the amount of diluent used is well in excess of that required to satisfy the azeotrope, so that complete removal of glycidol from the column underflow of column 36 is insured by operating so that a small excess of diluent over the azeotropic requirement is removed with the glycidol. The glycidol-azeotrope leaves through line 55 and goes to the recovery unit. The underflow from column 36 flows through line 56 to column 38 where the diluent is removed overhead through line 60 and returned to the process. High boilers are removed as an underflow from column 38.

The glycidol-diluent azeotrope recovered from column 36 through line 55 may be treated in several ways. Pure glycidol can be separated by breaking the azeotrope and separating glycidol for use as a chemical intermediate. The azeotropic mixture can be subjected directly to hydrolysis conditions if the solvent selected is stable under the conditions of hydrolysis employed and separable from the hydrolysate. Hydrolysis of the azeotropic mixture proceeds readily; the glycerol partitions into the aqueous phase so that the diluent can be decanted off for recycle to the system leaving the aqueous phase to be concentrated and the glycerol subsequently refined.

Figure 3:
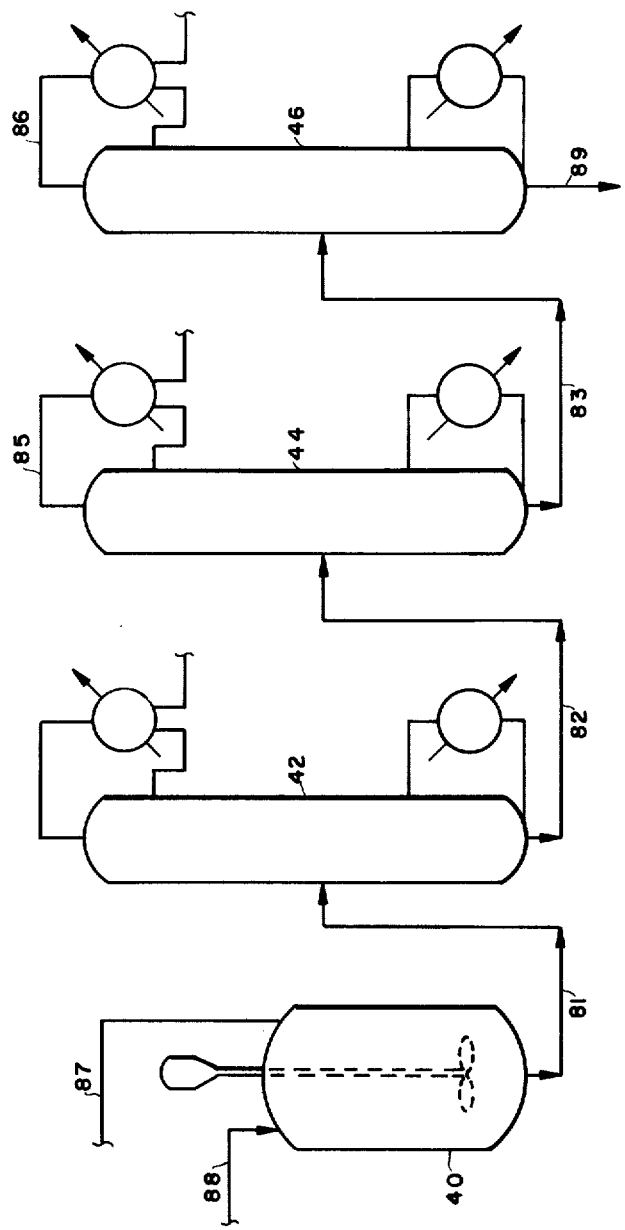
FIG. 3 is a schematic diagram for the process using a high boiling solvent and no diluent, but omitting the hydrolysis step.

The process employing a high boiling solvent and no diluent is described with reference to FIG. 3. Allyl alcohol is fed to reactor 40 through line 88. Peracetic acid at 5 to 40% weight concentration in an inert high boiling solvent boiling between 125° and 180°C. such as diisobutyl ketone, is fed through line 87 to reactor 40 where the reaction mixture is maintained at a temperature between 35° and 70°C. The peracetic acid solution usually contains 5 to 10% acetic acid. An excess of alcohol is preferred. After the epoxidation reaction is carried out the reaction mixture is subjected to a sequence of continuous distillations below 400 mm Hg to rapidly and continuously separate co-product acetic acid from glycidol and then recover glycidol; thus the mixture is then fed from the epoxidizer through line 81 to column 42 wherein acetic acid, surviving peracetic acid and allyl alcohol are removed overhead. This column is kept operating at an overhead pressure of about 40 mm. of Hg., a feed plate temperature of about 75°C. and reboiler temperature of about 92°C. when using diisobutyl ketone as the solvent. The glycidol-high boiling solvent solution is removed from column 42 as an underflow through line 82 and fed to column 44.

Reaction between glycidol and acetic acid is largely prevented by the fact that in column 42 the products acetic acid and glycidol are rapidly and continuously separated.

In column 44, when using diisobutyl ketone as the solvent, the column is operated with an overhead pressure of about 50 mm. of Hg. and a vapor temperature of about 78°C. when the reboiler is operated at about 88° to 92°C. Glycidol is removed as a vapor through line 85. When diisobutyl ketone is used as the solvent, the glycidol is obtained in the form of the azeotrope with diisobutyl ketone. The glycidol-solvent mixture may be fed directly to the hydrolyzer along with the requisite amount of water, and the mixture held at reaction temperature until hydrolysis is complete. The mixture is then cooled and, when diisobutyl ketone is used as the solvent, the solvent is decanted from the aqueous glycerol mixture and returned to the process. The glycerol is concentrated and refined by conventional methods. The glycidol-solvent mixture leaving column 44 through line 85 can, if desired, be processed to recover product glycidol.

The underflow from column 44 containing solvent leaves through line 83 and is fed to column 46. Column 46 is operated to separate the solvent, which is returned to the process, from high boilers which leave the process through line 89.

The processes of this invention are further illustrated in the following examples which are given by way of example and not by way of limitation to illustrate the invention to those skilled in the art. All parts and percentages are by weight unless otherwise specified.

EXAMPLE 1

The equipment consisted of a 12-liter resin flask fitted with an aluminum cooling coil, containing a seven-neck head equipped with a condenser, mechanical stirrer, thermometer, two addition funnels, and the inlet and outlet for the cooling coil. The charge consisted of about 12 moles of peracetic acid as a 15–30% solution in acetone containing 6–8% acetic acid and the appropriate quantity of allyl alcohol, as shown in the table. The peracetic acid and allyl alcohol were added to the reactor simultaneously through the addition funnels over a period of 39 minutes. The reactant ratios, temperatures, reaction time, allyl alcohol conversions, and glycidol yields (based on allyl alcohol) are given in the following table:

| | Moles allyl alcohol per mole peracid | Time, hours | Peracetic Conc. % | Temp. °C. | Allyl alcohol conversion, % | Glycidol Yield, % |
|---|---|---|---|---|---|---|
| A | 0.77 | 2.0 | 19.8 | 69 | 92.7 | 94.5 |
| B | 1.3 | 3.0 | 20.3 | 55 | 65.1 | 95.8 |
| C | 1.3 | 4.0 | 15.0 | 55 | 64.2 | 92.6 |
| D | 2.0 | 6.0 | 20.6 | 45 | 45.9 | 100. |
| E | 3.0 | 3.75 | 30.0 | 55 | 31.8 | 100. |

F. Three hundred and forty-six parts of a solution obtained from A of this example were fed at 3.5 milliliters per minute to the mid-point of a rectification column operated at 100 millimeters Hg. pressure. The acetone was taken off overhead and contained less than one percent acetic acid and no glycidol. The underflow from the column contained 98% of the glycidol fed to the column. This crude glycidol was then fed to a column operated at 29 millimeters Hg. Acetic acid was removed overhead together with unconverted allyl alcohol. The high boiling components were withdrawn from the bottom, and at a level one plate above the reboiler section a vapor was withdrawn and condensed to give glycidol containing one percent acetic acid, representing 98.5% of the glycidol in the feed.

G. A mixture of 432 parts of water, one part of 90% formic acid and 72 parts of glycidol obtained from operation F of this example was heated at 60°C. for 4 hours at which time all the glycidol had been consumed. Water was then removed by evaporation and the glycerol was distilled through a short column at 15 millimeters Hg. The fraction distilling over the range of 167°–172°C. consisted of 86 parts and represented a 96% yield of glycerol based on the glycidol charged. The product obtained in this manner meets commercial specifications.

Similar results are obtained using this procedure by substituting for acetone: ethyl acetate, methylal, benzene and chloroform.

EXAMPLE 2

An epoxidation vessel was charged with allyl alcohol (2668 g., 99.1 percent assay, 45.52 moles) which was heated to 45°C. To this was added a solution of peracetic acid in acetone (5390 g. of 21.4 percent peracetic acid, 15.18 moles) during 10 minutes while cooling to maintain a temperature of 45°C. The mixture was then held at 45°C and sampled at intervals to determine the conversion of peracetic acid. After approximately three hours, the peracetic acid conversion was 93.9 percent; 13.71 moles of allyl alcohol had been consumed and 13.01 moles of glycidol appeared for an alcohol reaction efficiency of 94.9 percent. The mixture was held for an additional hour at 45°C., then rapidly cooled to 12°C.

The epoxidation mixture (7444 g.) was diluted with pseudocumene (3722 g.) and the mixture was fed, at a rate of 62.1 g/minute to a 2-inch Oldershaw distillation column, constituted in descending order as follows: refrigerated condenser, magnetic reflux head, 10-tray section, feed section, five-tray section, temperature sensor, reboiler.

Feed composition was as follows:

| Component | Weight percent |
|---|---|
| Acetone | 33.3 |
| Allyl alcohol | 14.8 |
| Acetic acid | 9.77 |
| Glycidol | 8.09 |
| High boilers | 0.67 |
| Pseudocumene | 33.3 |

Pressure at the top of the column was 75 mm. Hg.; column temperatures were: overhead vapor, 6°–6.5°C.; feed plate, 32°–33.5°C.; reboiler, 61.5°–62.5°C. The reflux ratio was 1:1.

From a total feed of 11,166 g., there were obtained 3,664 g. of distillate and 7,502 g. of underflow of the following weight percent compositions:

| Component | Distillate, 3,664 g. | Underflow, 7,502 g. |
|---|---|---|
| Acetone | 98.1 | 0.8 |
| Allyl alcohol | 0.8 | 21.6 |
| Acetic Acid | 0.02 | 14.43 |
| Glycidol | 0.1 | 11.84 |
| Pseudocumene | — | 50.3 |
| Unidentified | 1.0 | — |
| High boilers | — | 1.0 |

Recovery of glycidol was 98.3 percent.

The underflow (7,473 g.) from the acetone removal column was fed at a rate of 40 g./minute to a 2-inch Oldershaw column constituted as follows: water-cooled condenser, magnetic reflux head, 10-tray section, temperature sensor, 10-tray section, feed section, 25 tray section, reboiler.

Pressure at the top of the column was 50 mm. of Hg.; reflux ratio was 1:1. Column temperatures were: overhead vapor, 47.5°C.; 10th tray 51.5°C.; feed tray 60°C.; reboiler 90°C. Column effluent weight percent compositions were as follows:

| Component | Distillate (2,768 g.) | Underflow (4,802 g.) |
|---|---|---|
| Acetic acid | 34.78 | 1.27 |
| Glycidol | 0.15 | 18.28 |
| Pseudocumene | 4.4 | 78.8 |
| High boilers | — | 1.6 |
| Allyl Alcohol | 58.31 | — |
| Acetone | 2.17 | — |

Recovery of glycidol across this column was 99.2 percent.

Recovery of glycidol azeotrope from the underflow of the acetic acid removal column was achieved by feeding the underflow to a 1-inch Oldershaw column constituted in descending order as follows: water-cooled condenser, magnetic reflux head (set at 1:1), five-trays, feed section, five-trays, reboiler. At a column head pressure of 60 mm., the vapor temperature was 75.5°C., the reboiler temperature was 89°C. From 4,160 g. of feed, there were obtained 2,082 g. of distillate containing 33.0 percent glycidol and 2,050 g. of underflow containing 2.56 percent glycidol.

EXAMPLE 3

Epoxidation was conducted by reacting allyl alcohol with 15 percent peracetic acid in acetone at a ratio of 1.3 moles allyl alcohol/mole of peracetic acid. Peracetic acid conversion was carried to 90 percent. The reaction mixture was then diluted with pseudocumene to give a mixture which was fed to an acetone removal column. In the following discussion, each component rate through the system is shown in pounds per hour.

The column consisted of: water-cooled condenser, reflux head (1:1 reflux), 10-trays, feed section, 10-trays, reboiler. Overhead pressure was 400 mm. Hg., temperature 40°C.; reboiler pressure was 415 mm. Hg., temperature 109°C. Feed composition (lb/hr.) was: acetone, 24.13; allyl alcohol, 1,382; peracetic acid, 0.452; acetic acid, 4,722; glycidol, 3.767; high boilers, 0.200; pseudocumene, 30.13. Overhead was taken: acetone, 24.08; allyl alcohol, 0.121. The underflow consisted of: acetone, 0.042; allyl alcohol, 0.915; peracetic acid, nil; acetic acid, 5.080; glycidol, 4.169; high boilers, 0.243; pseudocumene, 30.13.

The underflow from the acetone removal column was fed to the acetic acid removal column, consisting of: water-cooled condenser, reflux head (2:1 reflux ratio), 30-trays, feed section, 20-trays, reboiler. Overhead pressure was 50 mm. Hg., temperature 46.5°C.; reboiler pressure was 88 mm. Hg., temperature, 90°C. Overhead was taken: acetone, 0.042; allyl alcohol, 0.915; acetic acid, 5.011; glycidol, 0.0065; pseudocumene, 0.314. The underflow consisted of: acetic acid, 0.0684; glycidol, 4.15; high boilers, 0.255; pseudocumene, 29.82.

The underflow from the acetic acid removal column was fed to the glycidol azeotrope column which consisted of: water-cooled condenser, reflux head (2:1 reflux ratio), five-trays, feed section, 10-trays. Overhead pressure was 60 mm. Hg., temperature, 80°C.; reboiler pressure was 70 mm. Hg., temperature 93°C. Overhead was taken: acetic acid, 0.0684; glycidol, 4.150; pseudocumene, 8.428. The underflow consisted of high boilers, 0.255; pseudocumene, 21.39.

Pseudocumene was recovered from the underflow for recycle by simple distillation.

EXAMPLE 4

A solution of peracetic acid, 7.70 percent (32.1 moles), and acetic acid, 3.55 percent (20.6 moles) in diisobutyl ketone was treated with allyl alcohol (41.7 moles) at 50°C. for 2.5 hours, then held at 57°–58°C. for another 3 hours. At the end of this time, the conversion of peracetic acid was 94.0 percent with an indicated reaction efficiency to glycidol of 92.4 percent based on allyl alcohol and 86.2 percent based on peracetic acid.

The epoxidation mixture was fed at a rate of 35.8 g./min. to a 2-inch Oldershaw column constituted as follows: water-cooled condenser, reflux head (6:1 reflux ratio), 10-trays, temperature sensor, 10-trays, feed section, 30-trays, reboiler. Overhead pressure was 38 mm. Hg., temperature, 35.5°–36.0°C. Feed-plate temperature was 74°C., reboiler temperature, 91.5°–92°C.

Approximately 12.5 percent of the feed was taken overhead and contained the following: allyl alcohol, 13.46 moles; acetic acid, 50.55 moles, corresponding to an efficiency of 94.9 percent based on total acids charged to the epoxidation.

The underflow from the acetic acid removal column, containing 0.14 percent acetic acid, was fed at 44 g./min. to the glycidol azeotrope column which consisted of a 2-inch Oldershaw, arranged as follows: water-cooled condenser, reflux head (2:1 reflux ratio), five-trays, feed section, 10-trays, reboiler. Overhead pressure was 50 mm. Hg. and the vapor temperature was 77.5°–78°C. The reboiler operated at 89°–91°C. Approximately 28.5 percent of the feed was taken overhead, and contained 29.9 percent glycidol (corresponding to 25.03 moles), 0.48 percent acetic acid. Only 0.03 percent glycidol was contained in the underflow.

The recovery of glycidol corresponds to an efficiency of 88.7 percent based on unrecovered allyl alcohol.

The underflow from the glycidol azeotrope column was flash distilled to recover the diisobutyl ketone for recycle.

EXAMPLE 5

An agitated reaction vessel was charged with 9,125 g. of water which was heated to reflux. To this was added at a rate of 50 ml./min. 3,050 g. of a solution of glycidol (29.92%, 912.5 g., 12.33 moles) and acetic acid (0.35%, 10.7 g., 0.178 mole) in diisobutyl ketone which had been obtained by azeotropic distillation. After completion of the glycidol addition, the mixture was held under reflux for another 3 hours. After cooling, the diisobutyl ketone layer which separated was decanted from the aqueous glycerol and recycled to the process. The glycerol content of the aqueous hydrolysate was 10.9 percent corresponding to a crude yield of 96 percent. The pH of the solution was adjusted by the addition of 0.2 mole of sodium hydroxide, and the solution was concentrated to give 1,172 g. of crude glycerol. This was distilled at reduced pressure to give refined glycerol meeting commercial specifications.

As will be apparent to those skilled in the art, numerous modifications and variations of the embodiments illustrated above may be made without departing from the spirit of the invention or the scope of the following claims.

What is claimed is:

1. A process for epoxidizing allyl alcohol consisting essentially of (a) in a reaction zone, epoxidizing allyl alcohol at a temperature between 25° and 100°C., using peracetic acid in solution in a substantially anhydrous, inert, organic solvent boiling between 125° and 180°C., containing between 5 and 40% peracetic acid, the molar ratio of allyl alcohol to peracetic acid being more than one and less than 5, until at least 70 to about 95% of the peracetic acid is reacted to produce a reaction mixture containing glycidol, allyl alcohol, peracetic acid, co-product acetic acid and said solvent (b) subjecting the reaction mixture to continuous fractional distillation below 400 mm. of Hg., to rapidly and continuously separate (1) a mixture of co-product acetic acid with allyl alcohol and surviving peracetic acid from (2) a mixture of glycidol and said solvent, said mixture (1) being more volatile in said distillation than said mixture (2).

2. Process which consists essentially of the steps recited in claim 1 and the subsequent step of then mixing the mixture of glycidol and solvent with between 10 and 100 moles of water per mixture of mole of glycidol, holding the glycidol-water-solvent mixture to a temperature of between 25° and 170°C. to hydrolyze glycidol to glycerol and thereafter recovering glycerol.

3. Process as in claim 1 in which said reaction zone is at a temperature of about 40° to 65°C.

4. Process as in claim 3 in which said solvent is one which forms an azeotrope with glycidol.

5. Process as in claim 1 in which said solvent is diisobutyl ketone.

* * * * *